(12) United States Patent
Woloszko et al.

(10) Patent No.: US 11,523,864 B2
(45) Date of Patent: *Dec. 13, 2022

(54) METHODS AND SYSTEMS RELATED TO AN ELECTROSURGICAL CONTROLLER

(71) Applicant: ArthroCare Corporation, Austin, TX (US)

(72) Inventors: Jean Woloszko, Austin, TX (US); Scott A. Armstrong, Wimberley, TX (US); Michael Bozeman, Round Rock, TX (US); Christopher A. Wallis, Austin, TX (US)

(73) Assignee: ArthroCare Corporation, Austin, TX (US)

( * ) Notice: Subject to any disclaimer, the term of this patent is extended or adjusted under 35 U.S.C. 154(b) by 350 days.

This patent is subject to a terminal disclaimer.

(21) Appl. No.: 16/545,202

(22) Filed: Aug. 20, 2019

(65) Prior Publication Data

US 2019/0374284 A1 Dec. 12, 2019

Related U.S. Application Data

(63) Continuation of application No. 14/181,281, filed on Feb. 14, 2014, now Pat. No. 10,420,607.

(51) Int. Cl.
*A61B 18/12* (2006.01)
*A61B 18/18* (2006.01)
*A61B 18/00* (2006.01)

(52) U.S. Cl.
CPC .......... *A61B 18/18* (2013.01); *A61B 18/1206* (2013.01); *A61B 2018/00666* (2013.01);
(Continued)

(58) Field of Classification Search
CPC ...... A61B 18/1206; A61B 2018/00678; A61B 2018/00708; A61B 2018/00761; A61B 2018/00666
See application file for complete search history.

(56) References Cited

U.S. PATENT DOCUMENTS

2007/0129716 A1* 6/2007 Daw .................. A61B 18/1402
606/34
2010/0179538 A1* 7/2010 Podhajsky ......... A61B 18/1206
606/35

OTHER PUBLICATIONS

Korean Application No. 10-2016-7025025—KIPO'S Notice of Preliminary Rejection dated Mar. 12, 2021.
(Continued)

*Primary Examiner* — Jaymi E Della
(74) *Attorney, Agent, or Firm* — Norman F. Hainer, Jr.

(57) ABSTRACT

An electrosurgical controller and related methods. At least some of the illustrative embodiments are methods including: placing a distal end of an electrosurgical wand in operational relationship with biological tissue; delivering energy to an active electrode of the electrosurgical wand. During delivering energy, the method may comprise: measuring a value indicative of flow of the energy to the active electrode; summing, over a first predetermined window of time, to create a first value indicative of energy provided to the active electrode; summing, over a second predetermined window of time, to create a second value indicative of energy provided to the active electrode. The method may further comprise: ceasing delivering energy responsive to the first value meeting or exceeding a predetermined value; and ceasing delivering energy responsive to the second value meeting or exceeding a threshold value.

17 Claims, 7 Drawing Sheets

(52) U.S. Cl.
CPC ............... *A61B 2018/00678* (2013.01); *A61B 2018/00708* (2013.01); *A61B 2018/00761* (2013.01); *A61B 2018/00779* (2013.01); *A61B 2018/00827* (2013.01); *A61B 2018/00892* (2013.01)

(56) References Cited

OTHER PUBLICATIONS

AU Office Action for App No. 2019257435 dated Mar. 20, 2020, 3 pages.
Chinese Application No. 201910973366.X Text of Second Office Action & Search Report dated May 27, 2022.
Chinese Application No. 201910973366.X Search Report & Text of First Office Action dated Mar. 3, 2022.

* cited by examiner

METHODS AND SYSTEMS RELATED TO AN ELECTROSURGICAL CONTROLLER

CROSS-REFERENCE TO RELATED APPLICATIONS

This application is a continuation of application Ser. No. 14/181,281 filed Feb. 14, 2014, now U.S. Pat. No. 10,420,607, which is herein incorporated by reference in its entirety.

BACKGROUND

Electrosurgical systems are used during surgical procedures to remove several different tissue types. For example, procedures involving the knee or shoulder may remove portions of cartilage, meniscus, and free floating and/or trapped tissue. In some cases, the removal may be a very slight removal, such as tissue sculpting, and in other cases more aggressive removal of tissue is used. Electrosurgical systems may also operate in a coagulation mode, to seal arterial vessels exposed during tissue removal, and sealing to reduce bleeding.

Regardless of whether the electrosurgical system is used for tissue removal or for coagulation, electrosurgical systems may conform to certain standards set by standard setting organizations (e.g., International Electrotechnical Commission (IEC)) that limit the amount of energy over time that can be applied as part of the procedure.

Any advance that increases performance of electrosurgical systems, yet still enables the electrosurgical system to conform to the various standards, would provide a competitive advantage.

BRIEF DESCRIPTION OF THE DRAWINGS

For a detailed description of exemplary embodiments, reference will now be made to the accompanying drawings in which.

NOTATION AND NOMENCLATURE

Figure 1:
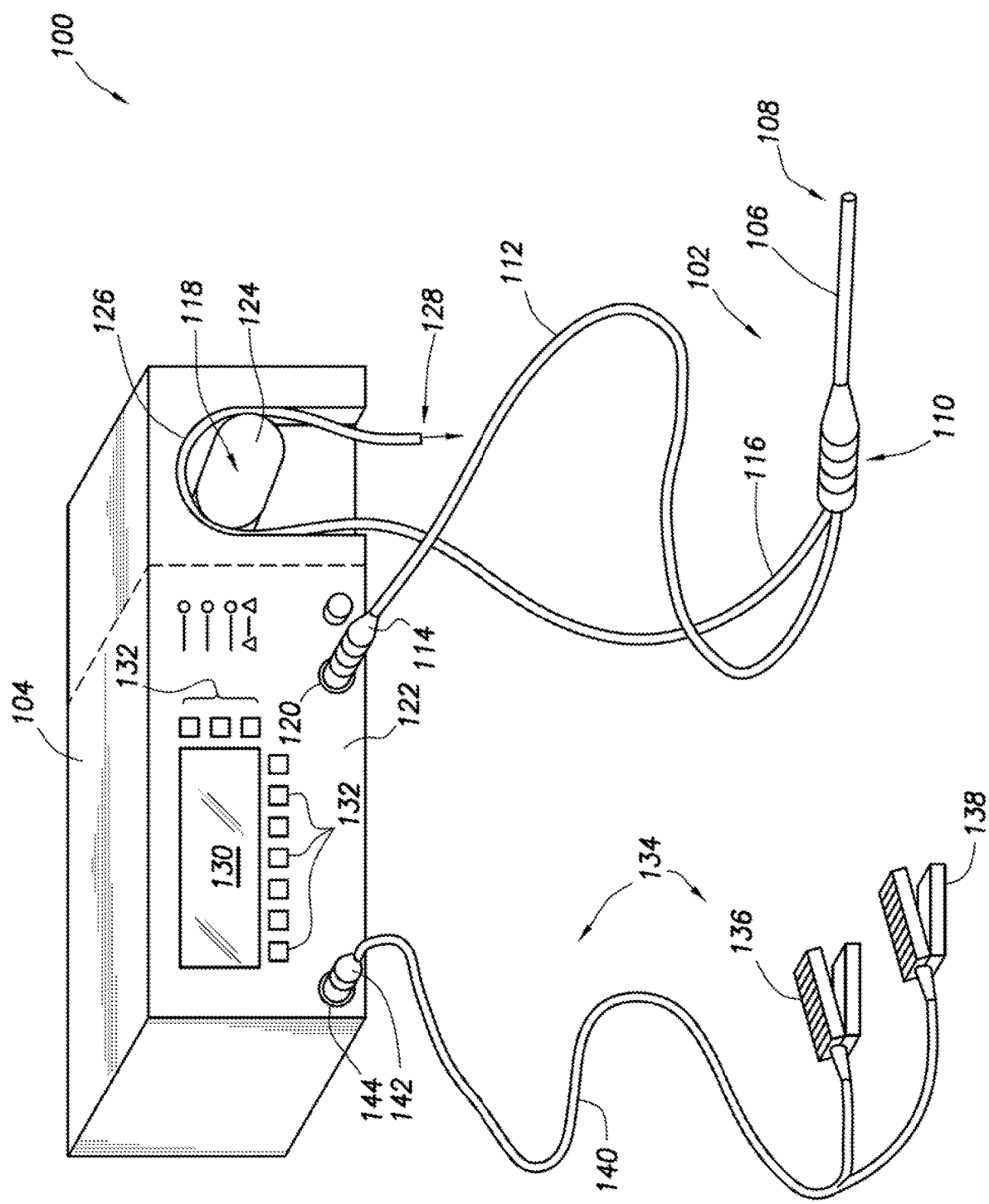
FIG. 1 shows an electrosurgical system in accordance with at least some embodiments.

Certain terms are used throughout the following description and claims to refer to particular system components. As one skilled in the art will appreciate, companies that design and manufacture electrosurgical systems may refer to a component by different names. This document does not intend to distinguish between components that differ in name but not function.

In the following discussion and in the claims, the terms "including" and "comprising" are used in an open-ended fashion, and thus should be interpreted to mean "including, but not limited to . . . ." Also, the term "couple" or "couples" is intended to mean either an indirect or direct connection. Thus, if a first device couples to a second device, that connection may be through a direct connection or through an indirect connection via other devices and connections.

Reference to a singular item includes the possibility that there are plural of the same items present. More specifically, as used herein and in the appended claims, the singular forms "a," "an," "said" and "the" include plural references unless the context clearly dictates otherwise. It is further noted that the claims may be drafted to exclude any optional element. As such, this statement serves as antecedent basis for use of such exclusive terminology as "solely," "only" and the like in connection with the recitation of claim elements, or use of a "negative" limitation. Lastly, it is to be appreciated that unless defined otherwise, all technical and scientific terms used herein have the same meaning as commonly understood by one of ordinary skill in the art to which this invention belongs.

"Ablation" shall mean removal of tissue based on tissue interaction with a plasma.

"Plasma" shall mean a low temperature highly ionized gas formed within vapor bubbles or a vapor layer that is capable of emitting an ionized discharge.

"Active electrode" shall mean an electrode of an electrosurgical wand which produces an intended electrically-induced tissue-altering effect when brought into contact with, or close proximity to, a tissue targeted for treatment.

"Return electrode" shall mean an electrode of an electrosurgical wand which serves to provide a current flow path for electrical charges with respect to an active electrode, and/or an electrode of an electrical surgical wand which does not itself produce any intended electrically-induced tissue-altering effect on tissue targeted for treatment.

A proximity that is in "operational relationship with biological tissue" shall mean a proximity wherein the tissue interacting with a plasma affects the impedance presented by the plasma to electrical current flow through the plasma.

Where a range of values is provided, it is understood that every intervening value, between the upper and lower limit of that range and any other stated or intervening value in that stated range is encompassed within the invention. Also, it is contemplated that any optional feature of the inventive variations described may be set forth and claimed independently, or in combination with any one or more of the features described herein.

All existing subject matter mentioned herein (e.g., publications, patents, patent applications and hardware) is incorporated by reference herein in its entirety except insofar as the subject matter may conflict with that of the present invention (in which case what is present herein shall prevail). The referenced items are provided solely for their disclosure prior to the filing date of the present application. Nothing herein is to be construed as an admission that the present invention is not entitled to antedate such material by virtue of prior invention.

The disclosure draws a distinction between energy delivery over time (e.g., number of Joules delivered in one second, or the number of Joules delivered in a range between 30 and 500 milliseconds) and energy delivery rate (e.g., Joules/second). Thus, there is a difference between an example 400 Joules delivered over one second, and an example rate of 400 Joules/second (i.e., 400 Watts). One could delivery energy at a rate exceeding 400 Watts in short bursts less of than one second, yet not exceed the example 400 Joules delivered over one second.

DETAILED DESCRIPTION

Before the various embodiments are described in detail, it is to be understood that this invention is not limited to particular variations set forth herein as various changes or modifications may be made, and equivalents may be substituted, without departing from the spirit and scope of the invention. As will be apparent to those of skill in the art upon reading this disclosure, each of the individual embodiments described and illustrated herein has discrete components and features which may be readily separated from or combined with the features of any of the other several embodiments without departing from the scope or spirit of the present invention. In addition, many modifications may be made to adapt a particular situation, material, composition of matter, process, process act(s) or step(s) to the objective(s), spirit or scope of the present invention. All such modifications are intended to be within the scope of the claims made herein.

The various embodiments are directed to electrosurgical methods and related electrosurgical systems that more accurately, and more closely, conform to operational standards regarding energy delivery for electrosurgical procedures. More particularly, various example methods measure the flow of energy (e.g., in Joules) to an active electrode of an electrosurgical wand. During the flow of energy multiple integrators or accumulators are in operation that measure the amount of energy delivered (e.g., in Joules) in overlapping time windows. When the total amount of energy dissipated within any time window meets or exceeds a predetermined threshold, energy delivery is temporarily ceased (referred to as "pulsing"). The various example systems and methods were developed in the context of wet-field electrosurgical procedures (e.g., within a knee or shoulder) with volume-controlled aspiration, where the aspiration aperture resides near the active electrode. Thus, the specification that follows is based on the developmental context; however, the example methods and systems likewise find use in dry-field electrosurgical procedures (e.g., procedures on the skin, or within the nose and mouth), where aspiration volume is not controlled (e.g., a single suction pressure is applied regardless of mode or volume flow), and also find use in situations where aspiration is provided from other surgical instruments separate and apart from the instrument carrying an active electrode. The specification first turns to an example system to orient the reader, then to a description of operation of related-art devices, and finally to a description of methods and systems in accordance with example embodiments.

FIG. 1 shows an electrosurgical system 100 in accordance with at least some embodiments. In particular, the electrosurgical system 100 comprises an electrosurgical wand 102 (hereinafter "wand 102") coupled to an electrosurgical controller 104 (hereinafter "controller 104"). The wand 102 comprises an elongate shaft 106 that defines distal end 108. The elongate shaft 106 further defines a handle or proximal end 110, where a physician grips the wand 102 during surgical procedures. The wand 102 further comprises a flexible multi-conductor cable 112 housing one or more electrical leads (not specifically shown in FIG. 1), and the flexible multi-conductor cable 112 terminates in a wand connector 114. As shown in FIG. 1, the wand 102 couples to the controller 104, such as by a controller connector 120 on an outer surface of the enclosure 122 (in the illustrative case of FIG. 1, the front surface).

Though not visible in the view of FIG. 1, in some embodiments the wand 102 has one or more internal fluid conduits coupled to externally accessible tubular members. As illustrated, the wand 102 has a flexible tubular member 116, used to provide aspiration at the distal end 108 of the wand. In accordance with various embodiments, the tubular member 116 couples to a peristaltic pump 118, which peristaltic pump 118 is illustratively shown as an integral component with the controller 104 (i.e., residing at least partially within the enclosure 122 of the controller 104). In other embodiments, an enclosure for the peristaltic pump 118 may be separate from the enclosure 122 for the controller 104 (as shown by dashed lines in the figure), but in any event the peristaltic pump is operatively coupled to the controller 104. In yet still further embodiments, suction for aspiration may be provided from any suitable source, such as suction outlets available in hospital settings. The example peristaltic pump 118 comprises a rotor portion 124 (hereafter just "rotor 124") as well as a stator portion 126 (hereafter just "stator 126"). The example flexible tubular member 116 couples within the peristaltic pump 118 between the rotor 124 and the stator 126, and movement of the rotor 124 against the flexible tubular member 116 causes fluid movement toward the discharge 128.

Still referring to FIG. 1, a display device or interface device 130 is visible through the enclosure 122 of the controller 104, and in some embodiments a user may select operational characteristics of the controller 104 by way of the interface device 130 and related buttons 132. For example, using one or more of the buttons 132 the surgeon may select among threshold energy values and/or adjustable time windows that control how often or how aggressively the system pulses during electrosurgical procedures. The various time windows and energy values are discussed more thoroughly below.

In some embodiments the electrosurgical system 100 also comprises a foot pedal assembly 134. The foot pedal assembly 134 may comprise one or more pedal devices 136 and 138, a flexible multi-conductor cable 140 and a pedal connector 142. While only two pedal devices 136 and 138 are shown, one or more pedal devices may be implemented. The enclosure 122 of the controller 104 may comprise a corresponding connector 144 that couples to the pedal connector 142. A physician may use the foot pedal assembly 134 to control various aspects of the controller 104, such as the mode of ablation. For example, pedal device 136 may be used for on-off control of the application of radio frequency (RF) energy to the wand 102. Further, pedal device 138 may be used to control and/or set the mode of operation of the electrosurgical system. For example, actuation of pedal device 138 may switch between ablation mode and coagulation mode.

The electrosurgical system 100 of the various embodiments implements ablation which employs Coblation® technology. In particular, the assignee of the present disclosure is the owner of Coblation® technology. Coblation® technology involves the application of a radio frequency (RF) signal between one or more active electrodes and one or more return electrodes of the wand 102 to develop high electric field intensities in the vicinity of the target tissue. The electric field intensities may be sufficient to vaporize an electrically conductive fluid over at least a portion of the one or more active electrodes in the region between the one or more active electrodes and the target tissue. The electrically conductive fluid may be inherently present in the body, such as blood, or in some cases extracelluar or intracellular fluid. In other embodiments, the electrically conductive fluid may be a liquid or gas, such as isotonic saline. In some embodiments, such as surgical procedures involving a knee or shoulder, the electrically conductive fluid is delivered in the vicinity of the active electrode and/or to the target site by a delivery system separate and apart from the system 100.

When the electrically conductive fluid is heated to the point that the atoms of the fluid vaporize faster than the atoms recondense, a gas is formed. When sufficient energy is applied to the gas, the atoms collide with each other causing a release of electrons in the process, and an ionized gas or plasma is formed (the so-called "fourth state of matter"). Stated otherwise, plasmas may be formed by heating a gas and ionizing the gas by driving an electric current through the gas, or by directing electromagnetic waves into the gas. The methods of plasma formation give energy to free electrons in the plasma directly, electron-atom collisions liberate more electrons, and the process cascades until the desired degree of ionization is achieved. A more complete description of plasma can be found in Plasma Physics, by R. J. Goldston and P. H. Rutherford of the Plasma Physics Laboratory of Princeton University (1995), the complete disclosure of which is incorporated herein by reference.

As the density of the plasma becomes sufficiently low (i.e., less than approximately 1020 atoms/cm$^3$ for aqueous solutions), the electron mean free path increases such that subsequently injected electrons cause impact ionization within the plasma. When the ionic particles in the plasma layer have sufficient energy (e.g., 3.5 electron-Volt (eV) to 5 eV), collisions of the ionic particles with molecules that make up the target tissue break molecular bonds of the target tissue, dissociating molecules into free radicals which then combine into gaseous or liquid species. By means of the molecular dissociation (as opposed to thermal evaporation or carbonization), the target tissue is volumetrically removed through molecular dissociation of larger organic molecules into smaller molecules and/or atoms, such as hydrogen, oxygen, oxides of carbon, hydrocarbons and nitrogen compounds. The molecular dissociation completely removes the tissue structure, as opposed to dehydrating the tissue material by the removal of liquid within the cells of the tissue and extracellular fluids, as occurs in related art electrosurgical desiccation and vaporization. A more detailed description of the molecular dissociation can be found in commonly assigned U.S. Pat. No. 5,697,882 the complete disclosure of which is incorporated herein by reference.

The energy density produced by electrosurgical system 100 at the distal end 108 of the wand 102 may be varied by adjusting a variety of factors, such as: the number of active electrodes; electrode size and spacing; electrode surface area; asperities and/or sharp edges on the electrode surfaces; electrode materials; applied voltage; current limiting of one or more electrodes (e.g., by placing an inductor in series with an electrode); electrical conductivity of the fluid in contact with the electrodes; density of the conductive fluid; and other factors. Accordingly, these factors can be manipulated to control the energy level of the excited electrons. Since different tissue structures have different molecular bonds, the electrosurgical system 100 may be configured to produce energy sufficient to break the molecular bonds of certain tissue but insufficient to break the molecular bonds of other tissue. For example, fatty tissue (e.g., adipose) has double bonds that require an energy level higher than 4 eV to 5 eV (i.e., on the order of about 8 eV) to break. Accordingly, the Coblation® technology in some modes of operation does not ablate such fatty tissue; however, the Coblation® technology at the lower energy levels may be used to effectively ablate cells to release the inner fat content in a liquid form. Other modes of operation may have increased energy such that the double bonds can also be broken in a similar fashion as the single bonds (e.g., increasing voltage or changing the electrode configuration to increase the current density at the electrodes). A more complete description of the various phenomena can be found in commonly assigned U.S. Pat. Nos. 6,355,032, 6,149,120 and 6,296,136, the complete disclosures of which are incorporated herein by reference.

Figure 2:
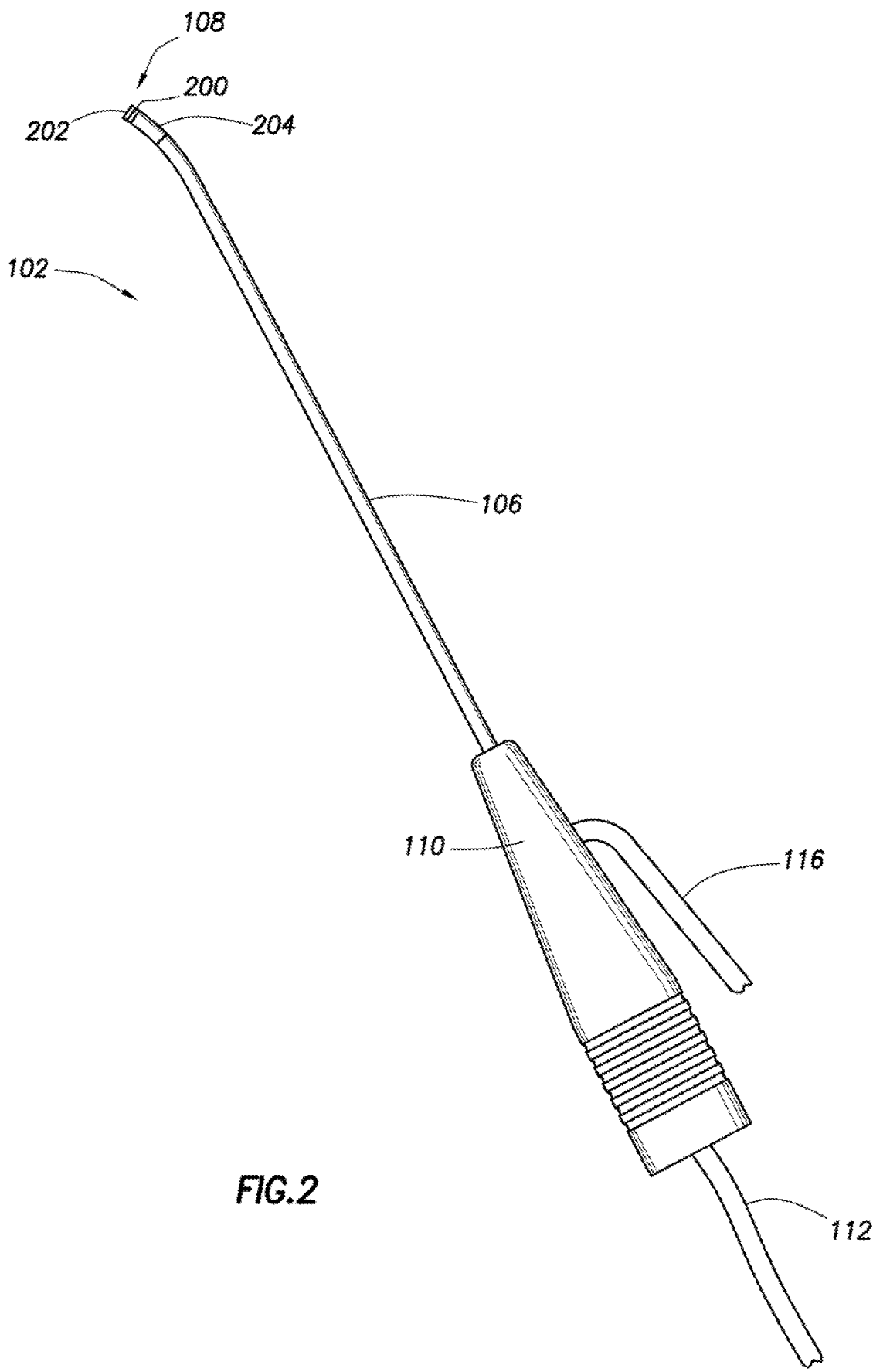
FIG. 2 shows an elevation view of an electrosurgical wand in accordance with at least some embodiments.

FIG. 2 shows an elevation view of wand 102 in accordance with example systems, and in particular a wet-field wand. The wand 102 comprises elongate shaft 106 which may be flexible or rigid, a handle 110 coupled to the proximal end of the elongate shaft 106, and an electrode support member 200 coupled to the distal end of elongate shaft 106. Also visible in FIG. 2 are the flexible tubular member 116 extending from the wand 102 and the multi-conductor cable 112. The wand 102 comprises an active electrode 202 disposed on the distal end 108 of the elongate shaft 106. Active electrode 202 may be coupled to an active or passive control network within controller 104 (FIG. 1) by means of one or more insulated electrical connectors (not shown) in the multi-conductor cable 112. The active electrode 202 is electrically isolated from a common or return electrode 204 which is disposed on the shaft proximally of the active electrode 202, in some example systems within 1 millimeter (mm) to 25 mm of the distal tip. Proximally from the distal tip, the return electrode 204 is concentric with the elongate shaft 106 of the wand 102. The support member 200 is positioned distal to the return electrode 204 and may be composed of an electrically insulating material such as epoxy, plastic, ceramic, silicone, glass or the like. Support member 200 extends from the distal end 108 of elongate shaft 106 (usually about 1 to 20 mm) and provides support for active electrode 202.

Figure 3:
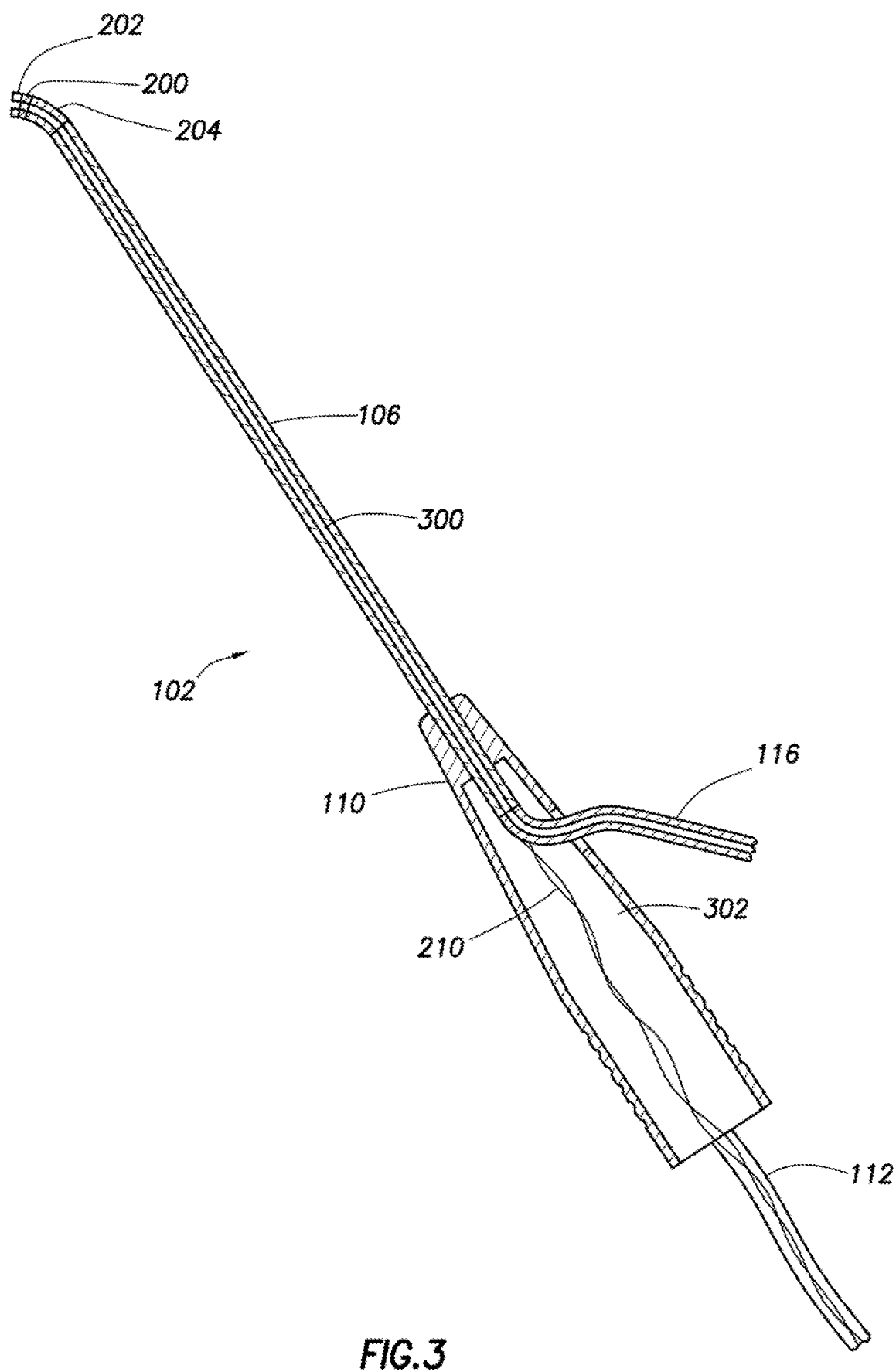
FIG. 3 shows a cross-sectional elevation view of an electrosurgical wand in accordance with at least some embodiments.

FIG. 3 shows a cross-sectional elevation view of the wand 102 in accordance with example embodiments. In particular, wand 102 comprises a suction lumen 300 defined within the elongate shaft 106. In the example wand 102 of FIG. 3, the inside diameter of the elongate shaft 106 defines the suction lumen 300, but in other cases a separate tubing within the elongate shaft 106 may define the suction lumen 300. The suction lumen 300 may be used for aspirating excess fluids, bubbles, tissue fragments, and/or products of ablation from the target site proximate to the active electrode 202. Suction lumen 300 extends into the handle 110 and fluidly couples to the flexible tubular member 116 for coupling to the peristaltic pump 118. Handle 110 also defines an inner cavity 302 within which electrical conductors 210 may reside, where the electrical conductors 210 may extend into the multi-conductor cable 112 and ultimately couple to the controller 104. The electrical conductors likewise extend through the elongate shaft and couple, one each, to the return electrode 204 and the active electrode 202, but the electrical conductors 210 are not shown to reside within the elongate shaft 106 so as not to unduly complicate the figure.

Figure 4:
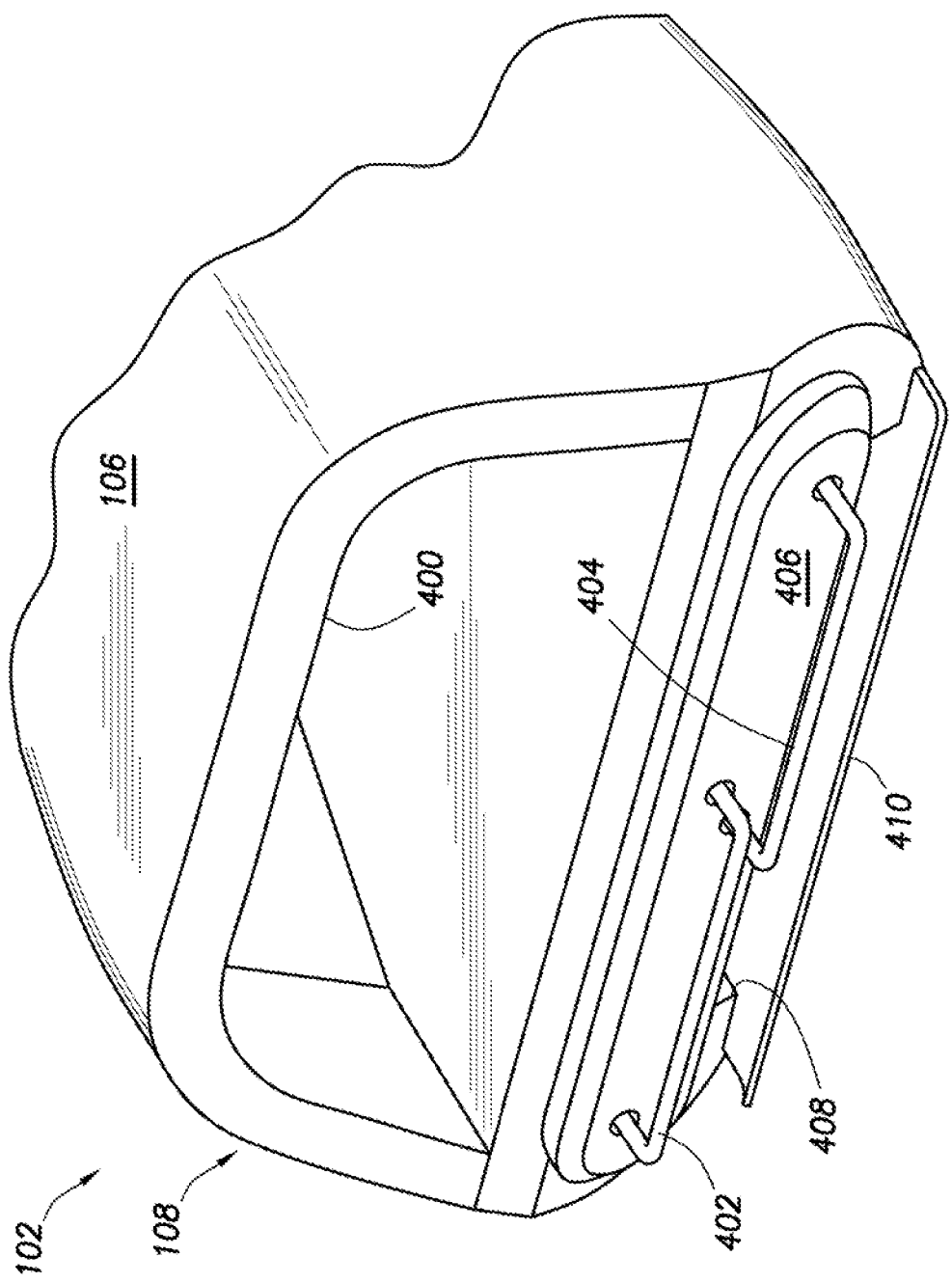
FIG. 4 shows a perspective view of a distal end of an electrosurgical wand in accordance with at least some embodiments.

FIG. 4 shows another example distal end 108 of wand, in this case for dry-field wand. In particular, FIG. 4 shows perspective view of the distal end 108 of wand that may be a wound care wand enabled for use to treat wounds on a patient's skin—a dry-field procedure. Other types of wands may be used, for example, the PROCISE® Max Plasma Wand available from ArthroCare Corporation of Austin, Tex., is designed and constructed for procedures associated with the mouth and throat—again, dry-field procedures. The relative proportions of the components of wands designed for different dry-field procedures will differ, but regardless of size and proportion wands for dry-field use will comprise the same base components: an active electrode; a return electrode; a source or discharge lumen from which conductive fluid flows; and a suction or aspiration lumen in which conductive fluid and ablated tissue is aspirated away from the treatment site.

The example distal end 108 of FIG. 4 has a suction lumen 400, two active electrodes 402 and 404, a support member 406, a source lumen 408, and return electrode 410. The support member 406 is coupled to the elongate housing 106. In a particular embodiment, the elongate housing 106 and handle 110 (FIG. 1) are made of a non-conductive plastic material, such as polycarbonate. In yet other embodiments, the handle 110 and/or elongate housing 106 may be constructed in whole or in part of metallic material, but the metallic material may be non-grounded and/or not provide a return path for electrons to the controller 104. Further, support member 406 is a non-conductive material resistant to degradation when exposed to plasma. In some cases support member 406 is made of a ceramic material (e.g., alumina ceramic), but other non-conductive materials may be equivalently used (e.g., glass).

An illustrative two active electrodes 402 and 404 are coupled to the support member 406. Each active electrode is a metallic structure, around which plasma is created during use in some operational modes. In some case, the wire is stainless steel, but other types of metallic wire (e.g., tungsten, titanium or molybdenum) may be equivalently used. As illustrated, each active electrode 402 and 404 is a loop of wire having a particular diameter. In wands designed for other uses (e.g., ablation of tissue of the soft palate), the active electrode may take the form of a screen or metallic plate with one or more apertures through the metallic plate leading to the suction lumen. Each example active electrode 402 and 404 is electrically coupled to the controller 104 (FIG. 1). In some cases, the active electrodes 402 and 404 are coupled to the controller by way of respective standoff portions and an insulated conductor (not specifically shown) that runs through the elongate housing 106. Thus, by way of the cable 112 (FIG. 1) and electrical pins (shown and discussed below) in the connector 114 (FIG. 1), the active electrodes 402 and 404 couple to the controller 104 (FIG. 1).

FIG. 4 further shows source lumen 408. The source lumen 408 is fluidly coupled within the elongate housing 106 to flexible tubular member, through which conductive fluids flow during use. Thus, during use, conductive fluid flows into the flexible tubular member, through one or more fluid conduits (not specifically shown) within the elongate housing 106, and out of the source lumen 408. The distal end 108 of the example wand of FIG. 4 further comprises a return electrode in the form of a conductive plate 410. In particular, the conductive plate 410 abuts the source lumen 408, and in the embodiments of FIG. 4 a portion of the conductive plate 410 at least partially defines the outer aperture of the source lumen 408. The conductive plate 410 is made of conductive material, which conductive material forms a return path for electrical current associated with energy applied to the active electrodes. In some cases the conductive plate 410 is made of stainless steel, but other types of metals (e.g., tungsten, molybdenum) may be equivalently used. The illustrative conductive plate 410 is oriented such that at least some of the saline flowing through the fluid conduit 408 contacts the conductive plate 410 before contacting an adjacent wound or contacting the active electrodes 402 and 404. Conductive plate 410 is electrically coupled to the controller 104 (FIG. 1). In some cases, the conductive plate 410 is coupled to the controller by way of an insulated conductor (not specifically shown) that runs through the elongate housing 106. Thus, by way of the cable 112 (FIG. 1) and electrical pins in the connector 114 (FIG. 1), the conductive plate 210 couples to the controller 104 (FIG. 1).

FIG. 4 also illustrates that the example dry-field wand further comprises a suction lumen 400. The suction lumen 400 is fluidly coupled to the flexible tubular member 116 (FIG. 1) by way of fluid conduit (not specifically shown) within the wand 102. Thus, and as the name implies, the suction lumen 204 is used to remove byproducts of wound treatment using the wand 102, such as removal of conductive fluid, molecularly disassociated tissue, and tissue separated from the wound but otherwise still intact. In example operation of a wand for wound care, aggressive aspiration is contemplated to enable removal of larger pieces of tissue not molecularly disassociated. The specification now turns to a more detailed description of the controller 104.

Figure 5:
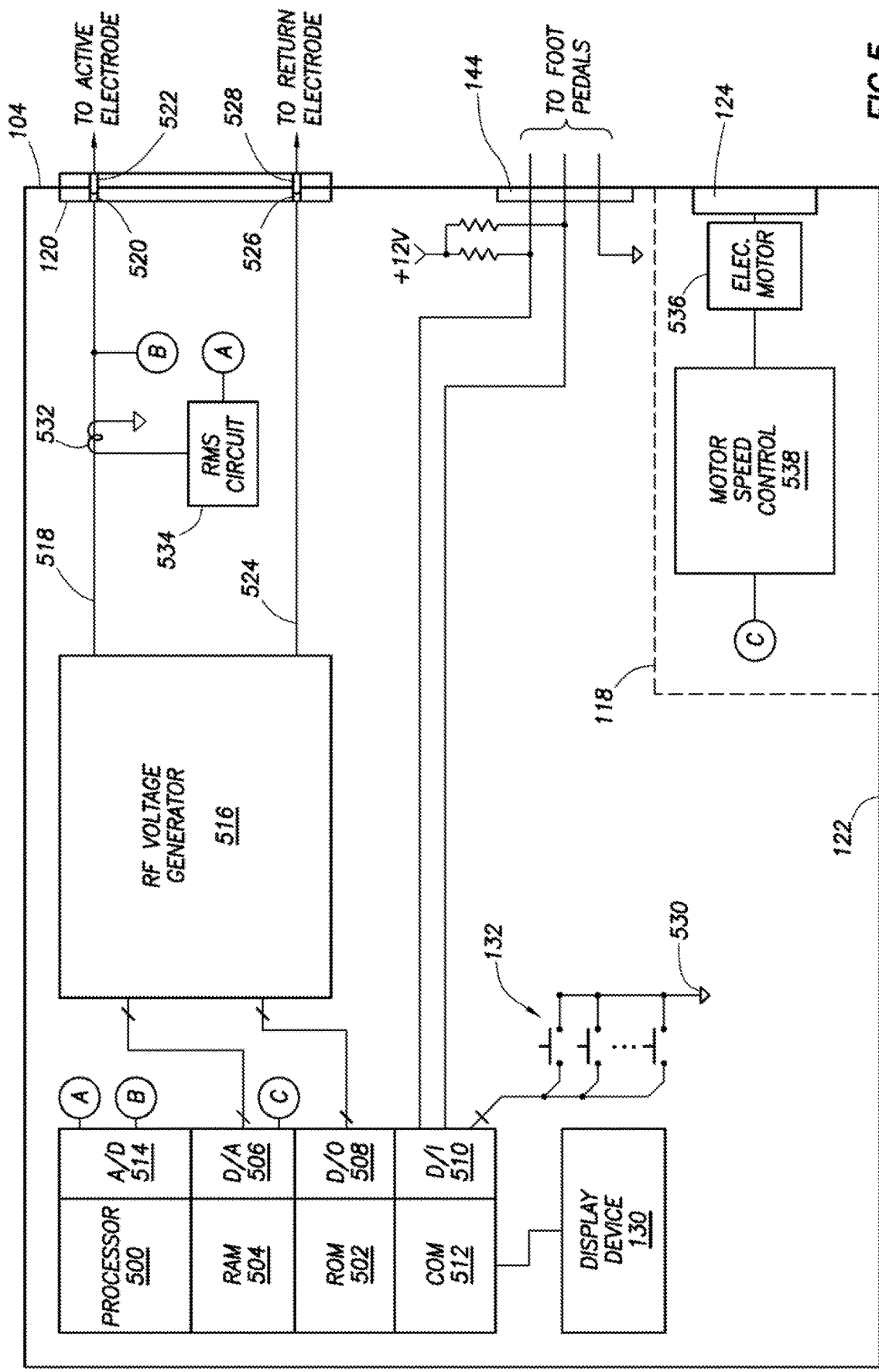
FIG. 5 shows an electrical block diagram of a controller in accordance with at least some embodiments.

FIG. 5 shows an electrical block diagram of controller 104 in accordance with at least some embodiments. In particular, the controller 104 comprises a processor 500. The processor 500 may be a microcontroller, and therefore the microcontroller may be integral with read-only memory (ROM) 502, random access memory (RAM) 504, flash or other non-volatile programmable memory, digital-to-analog converter (D/A) 506, analog-to-digital converter (A/D) 514, digital outputs (D/O) 508, and digital inputs (D/I) 510. The processor 500 may further provide one or more externally available peripheral busses (e.g., I²C, USB). The processor 500 may further be integral with communication logic 512 (e.g., UARTs, Ethernet enabled ports) to enable the processor 500 to communicate with external devices, as well as internal devices, such as display device 130. Although in some embodiments the processor 500 may be implemented in the form of a microcontroller, in other embodiments the processor 500 may be implemented as a standalone central processing unit in combination with individual RAM, ROM, communication, A/D, D/A, DO, DI devices, and communication hardware for communication to peripheral components. In some example systems, the processor 500 and related functionality are implemented as a MK60 series microcontroller available from Freescale Semiconductor of Austin, Tex.; however, other microcontrollers may be equivalently used.

ROM 502 (or possibly a flash memory) stores instructions executable by the processor 500. In particular, the ROM 502 may comprise a software program that, when executed, causes the processor to sum, over various time windows, energy delivery and when needed temporarily cease or "pulse" the energy provided to ensure the rate of energy delivery does not exceed predetermined thresholds (discussed more below). The RAM 504 may be the working memory for the processor 500, where data may be temporarily stored and from which instructions may be executed. Processor 500 couples to other devices within the controller 104 by way of the digital-to-analog converter 506 (e.g., in some embodiment the RF voltage generator 516), digital outputs 508 (e.g., in some embodiment the RF voltage generator 516), digital inputs 510 (e.g., interface devices such as push button switches 132 or foot pedal assembly 134 (FIG. 1)), and communication device 512 (e.g., display device 130).

Voltage generator 516 generates an alternating current (AC) voltage signal that is coupled to active electrode(s) (e.g., active electrode 202, active electrodes 402 and 404) of the example wands. In some embodiments, the voltage generator defines an active terminal 518 which couples to electrical pin 520 in the controller connector 120, electrical pin 522 in the wand connector 114, and ultimately to the active electrode(s). Likewise, the voltage generator defines a return terminal 524 which couples to electrical pin 526 in the controller connector 120, electrical pin 528 in the wand connector 114, and ultimately to the return electrode(s). Additional active terminals and/or return terminals may be used. The active terminal 518 is the terminal upon which the voltages and electrical currents are induced by the voltage generator 516, and the return terminal 524 provides a return path for electrical currents. In other embodiments the voltage generator 516 may be electrically "floated" from the balance of the controller 104, and thus the return terminal 524, when measured with respect to the common or earth ground (e.g., common 530) may show a voltage; however, an electrically floated voltage generator 516 and thus the potential for voltage readings on the return terminals 524 relative to earth ground does not negate the return terminal status of the terminal 524 relative to the active terminal 518.

The AC voltage signal generated and applied between the active terminal 518 and return terminal 524 by the voltage generator 516 is RF energy that, in some embodiments, has a frequency of between about 5 kilo-Hertz (kHz) and 20 Mega-Hertz (MHz), in some cases being between about 30 kHz and 2.5 MHz, in other cases being between about 50 kHz and 500 kHz, often less than 350 kHz, and often between about 100 kHz and 200 kHz. In some applications, a frequency of about 100 kHz is useful because target tissue impedance is greater at 100 kHz.

The RMS (root mean square) voltage generated by the voltage generator 516 may be in the range from about 5 Volts (V) to 1800 V, in some cases in the range from about 10 V to 500 V, often between about 10 V to 400 V depending on the mode of ablation and active electrode size. The peak-to-peak voltage generated by the voltage generator 516 for ablation in some embodiments is a square waveform in the range of 10 V to 2000 V, in some cases in the range of 100 V to 1800 V, in other cases in the range of about 28 V to 1200 V, and often in the range of about 100 V to 740 V peak-to-peak.

The voltage and current generated by the voltage generator 516 may be delivered as a square wave voltage signal or sine wave voltage with a sufficiently high frequency (e.g., on the order of 5 kHz to 20 MHz) such that the voltage is effectively applied continuously as compared with, e.g., lasers claiming small depths of necrosis, which are pulsed about 10 Hz to 20 Hz). In addition, the duty cycle of a square wave voltage produced by the voltage generator 516 is on the order of about 50% for some embodiments (e.g., half the time as a positive voltage square signal, and half the time as a negative voltage square signal) as compared with pulsed lasers which may have a duty cycle of about 0.0001%. Although square waves are generated and provided in some embodiments, the AC voltage signal is modifiable to include such features as voltage spikes in the leading or trailing edges of each half-cycle, or the AC voltage signal is modifiable to take particular shapes (e.g., sinusoidal, triangular).

The voltage generator 516 delivers average power levels ranging from several milliwatts to hundreds of watts per electrode, depending on the mode of operation and state of the plasma proximate to the active electrode(s). The voltage generator 516 in combination with the processor 500 are configured to set a constant root mean square (RMS) voltage output from the voltage generator 516 based on the mode of operation selected by the surgeon (e.g., one or more ablation modes, coagulation mode). A description of various voltage generators 516 can be found in commonly assigned U.S. Pat. Nos. 6,142,992 and 6,235,020, the complete disclosure of both patents are incorporated herein by reference for all purposes. Reference is also made to commonly assigned U.S. Pat. No. 8,257,350, titled "METHOD AND SYSTEM OF AN ELECTROSURGICAL CONTROLLER WITH WAVE-SHAPING", the complete disclosure of which is incorporated herein by reference as if reproduced in full below.

In some embodiments, the voltage generator 516 may be controlled by a program executing on the processor 500 by way of digital-to-analog converter 506. For example, the processor 500 may control the output voltages by providing one or more variable voltages to the voltage generator 516, where the voltages provided by the digital-to-analog converter 506 are proportional to the voltages to be generated by the voltage generator 516. In other embodiments, the processor 500 may communicate with the voltage generator by way of one or more digital output signals from the digital output converter 508, or by way of packet-based communications using the communication device 512 (the communication-based embodiments not specifically shown so as not to unduly complicate FIG. 5).

Still referring to FIG. 5, in some embodiment the controller 104 further comprises a mechanism to sense the electrical current provided to the active electrode. In the illustrative case of FIG. 5, sensing current provided to the active electrode may be by way of a current sense transformer 532. In particular, current sense transformer 532 may have a conductor of the active terminal 518 threaded through the transformer such that the active terminal 518 becomes a single turn primary. Current flow in the single turn primary induces corresponding voltages and/or currents in the secondary. Thus, the illustrative current sense transformer 532 is coupled to the analog-to-digital converter 514. In some cases, the current sense transformer may couple to the analog-to-digital converter 514 through amplification circuits, protection circuits, and/or circuits to convert the sensed values to RMS. In particular, in the example system of FIG. 5 the current sense transformer couples to an RMS circuit 534. RMS circuit 534 is an integrated circuit device that takes the indication of current from the current sense transformer 532, calculates a RMS value over any suitable period of time (in some example systems, over a 10 millisecond rolling window), and provides the RMS current values to the processor 500 through the analog-to-digital converter 514 (shown by bubble A). Other communicative couplings between the RMS circuit 534 and the processor 500 are contemplated (e.g., serial communication over an I$^2$C or USB pathway, Ethernet communication). The current sense transformer 532 is merely illustrative of any suitable mechanism to sense the current supplied to the active electrode, and other systems are possible. For example, a small resistor (e.g., 1 Ohm, 0.1 Ohm) may be placed in series with the active terminal 518, and the voltage drop induced across the resistor used as an indication of the electrical current. Given that the voltage generator 516 is electrically floated, the mechanism to sense current is not limited to the just the active terminal 518. Thus, in yet still further embodiments, the mechanism to sense current may be implemented with respect to the return terminal 524. For example, illustrative current sense transformer 532 may be implemented on a conductor associated with the return terminal 524.

In some example systems, the parameter used by the processor 500 with regard to ceasing energy flow to meet certain standards (again, discussed more below) is the electrical current flow. For example, in systems where the voltage generator 516 can accurately produce an output voltage independent of the impedance of the attached load, the processor 500 measuring electrical current flow and having set point control for the voltage created by the voltage generator 516 may be sufficient (e.g., to calculate a value indicative energy supplied to the active electrode). However, in other cases, voltage too may be a measured parameter. Thus, in some cases the active terminal 518 may be electrically coupled to the analog-to-digital converter 514 (as shown by bubble B). However, additional circuitry may be imposed between the active terminal 518 and the analog-to-digital converter 514, for example various step-down transformers, protection circuits, and circuits to account for the electrically floated nature of the voltage generator 516. Such additional circuitry is not shown so as not to unduly complicate the figure. In yet still other cases, voltage sense circuitry may measure the voltage, and the measured voltage values may be provided other than by analog signal, such as by way of packet-based communications over the communication port 512 (not shown so as not to unduly complicate the drawing).

Still referring to FIG. 5, controller 104 in accordance with example embodiments further comprises the peristaltic pump 118. The peristaltic pump 118 may reside at least partially within the enclosure 122. The peristaltic pump comprises the rotor 124 mechanically coupled to a shaft of the electric motor 536. In some cases, and as illustrated, the rotor of the electric motor may couple directly to the rotor 124, but in other cases various gears, pulleys, and/or belts may reside between the electric motor 536 and the rotor 124. The electric motor 536 may take any suitable form, such as an AC motor, a DC motor, and/or a stepper-motor. To control speed of the shaft of the electric motor 536, and thus to control speed of the rotor 124 (and the volume flow rate at the wand), the electric motor 536 may be coupled to a motor speed control circuit 538. In the illustrative case of an AC motor, the motor speed control circuit 538 may control the voltage and frequency applied to the electric motor 536. In the case of a DC motor, the motor speed control circuit 538 may control the DC voltage applied to the electric motor 536. In the case of a stepper-motor, the motor speed control circuit 538 may control the current flowing to the poles of the motor, but the stepper-motor may have a sufficient number of poles, or is controlled in such a way, that the rotor 124 moves smoothly. Stated otherwise, the rotor 124 moves smoothly due to the high number of steps per turn. The processor 500 couples to the motor speed control circuit 536, such as by way of the digital-to-analog converter 506 (as shown by bubble C).

The specification now turns to various standards to which the electrosurgical system may conform, and an explanation of how related-art devices attempt to conform to such standards. Electrosurgical systems in many cases are designed and constructed to conform to various standards set by standard setting organizations, such as the IEC. In the context of the current disclosure, the standard at issue is a limitation that an electrosurgical device should not provide to a patient more energy than 400 Joules over the course of one second. Related-art devices that utilize voltage or current generators that provide a substantially constant RMS voltage as between the active and return terminals merely implement an electrical current comparator system in order to ensure that the energy flow is not exceed. More particularly, related-art devices implement a comparator that compares a predetermined electrical current to the actual electrical current measured, and when the actual electrical current meets or exceeds the predetermined electrical current, the voltage generator is temporarily turned off (i.e., the power is "pulsed").

The predetermined electrical current value is selected based on the RMS voltage setting of the voltage generator. Consider, as an example, that a voltage generator of the related-art is commanded to create applied voltage of 400 V RMS. In the example situation of a setpoint voltage of 400 V RMS, related-art systems set a predetermined electrical current value of 1 Amp, and when the measured electrical current meets or exceeds 1 Amp, the pulsing is activated. Consider, as a second example, that a voltage generator of the related-art is commanded to create applied voltage of 200 V RMS. In the second example situation related-art systems set a predetermined electrical current value of 2 Amps, and when the measured electrical current meets or exceeds 2 Amps, pulsing is activated.

In order to highlight shortcomings of the related-art approach, consider again the example case of a setpoint voltage of the generator of 400 V RMS and a predetermined electrical current of 1 Amp. Assume, for purposes of discussion, that during a one second time period the actual electrical current is 0.5 Amp for 0.9 second of the one second time period, but in last 0.1 second the actual electrical current jumps to 1.1 Amps. In the example related-art systems, pulsing of the voltage generator is implemented because the electrical current exceeds 1.0 Amp, in spite of the fact that in the example situation the energy limit of 400 J over one second is not exceeded. Pulsing disrupts the electrosurgical procedure as ablation ceases during periods of time when the voltage generator is off, and re-establishing the plasma takes a finite amount of time.

Now consider the example situation "flipped". That is, consider a situation where over a one second time period actual electrical current is 1.1 Amp during the first 0.1 second, and then assume (with no control action taken responsive to the 1 Amp) the actual electrical current drops to 0.5 Amp for the remaining 0.9 second of the one second time period. Again, the example "flipped" situation the 400 Joule energy delivery over one second would not be exceeded; however, related-art comparator systems would none-the-less implement pulsing because the electrical current exceeds 1.0 Amp.

The example methods and systems of the current disclosure address, at least in the part, the shortcomings of the related-art comparator systems by implementing an integration and/or summing system where energy delivery over time is summed, and energy delivery is ceased when a predetermined value of summed energy is met or exceeded. Stated differently, the current disclosure describes the use of at least two different integration and/or summing systems instead of only one, so as to accurately limit the amount of energy delivered while providing instantaneously high power delivery that may be precisely adjusted as desired. This innovation serves to overcome the shortcoming of prior art systems with constant energy delivery time off on the occurrence of pulsing, whereas now energy delivery over time is adjustable in order to always be able to reach the maximum average power desired.

Further still, example systems implement multiple integration and/or summing systems, each summing system operable over distinct and at least partially coextensive (i.e., overlapping) windows of time, and each summing system utilizing different predetermined or threshold values. An example embodiment implements two summing systems: 1) a first summing system that tracks energy deliver over a rolling one second window, where the predetermined value over which pulsing is implemented set at 400 Joules (i.e., the one second window implementing the IEC standard limitation of no more than 400 Joules over a one second window); and 2) a second summing system tracking energy delivery over a rolling 20-500 millisecond window, where the threshold value (over which pulsing is implemented) is set at 5-400 Joules in some circumstances. Additional summing systems, adjustable predetermined and/or threshold values, and different predetermined values and/or threshold values are also contemplated. In example embodiments, the summing "systems" are implemented as programs executing on the processor 500, reading actual electrical current values (e.g., instantaneous, RMS), making energy calculations, and implementing pulsing when the energy delivery exceeds the predetermined or threshold values. However, the summing systems may be equivalently implemented with analog/digital hardware components.

In the example systems the controller 104, and more particularly programs executing on the processor 500, periodically read the actual electrical current supplied to the active electrode. In systems where the voltage generator 516 produces a substantially constant RMS voltage independent of the impedance of the active electrode circuit, the applied voltage may be assumed. In other cases, however, the processor may also periodically read applied voltage (e.g., instantaneous, RMS). In some systems, reading of actual electrical current (and perhaps applied voltage) takes place about every 1 millisecond, thus setting the base "interval" in the system as 1 millisecond; however, longer or shorter intervals between reading the values may be used. Based on the actual electrical current and applied voltage, an energy value is calculated for every interval, such as using the substantially the following equation:

$$E(t_n) = I(t_n) \times V(t_n) \times \Delta t \qquad (1)$$

where $E(t_n)$ is the energy delivered in an interval $t_n$ of time length $\Delta t$, $I(t_n)$ is the actual electrical current measurement for the interval, and $V(t_n)$ is the measured or assumed voltage for the interval. The energy delivery calculated for each interval is then used by the summing systems to determine energy value in the respective windows of time.

The example first summing system integrates and/or sums the energy delivery values $E(t_n)$ over a one second moving window, such as according the following equation:

$$E_{W1} = \sum_{t_w} E(t_n) \qquad (2)$$

where $E_{w1}$ is the energy value within the window $t_w$, where $t_w$ comprises two or more intervals $t_n$. In the case of the intervals spanning 1 millisecond and a one second moving window, approximately 1000 intervals may be summed to arrive at the $E_{w1}$ value. Equivalently, but stated in terms of the energy calculation within each interval, the energy delivery $E_{w1}$ over the example one second moving window may be calculated using substantially the following equation:

$$E_{W1} = \sum_{t_w} I(t_n) \times V(t_n) \times \Delta t \qquad (3)$$

again where $E_{w1}$ is the summed energy value within the window $t_w$, and again where $t_w$ comprises a two or more intervals $t_n$. In the case of the intervals spanning 1 millisecond and a one second moving window of time, approximately 1000 intervals may be summed to arrive at the $E_{w1}$ value.

Except for a period of time in which the electrosurgical controller has just been powered on, in most cases the integrators or summers will be summing in arrears. That is, the summed energy values will be values based on intervals spanning a window of time beginning in the past and up to and including the most recent interval. For example, consider the first summing system which integrates or sums to create a summed energy value over a one second window. For the first summing system, the energy delivery values are summed for each interval spanning the last one second. Once the next interval has elapsed and the next energy delivery value for the interval is calculated, the energy delivery value associated with the oldest interval in the time window is discarded and the newest energy delivery value associated with the newest interval is summed to create the next summed energy value. Thus, in some example systems a new summed energy value for the one second window of time is calculated every interval (e.g., calculated every 1 millisecond).

With each summed energy value calculated for a time window, the energy value is tested against a test value to determine whether the summed energy value in the specified time meets or exceeds the test value. In the case of the example first summing system with a one second window of time, the test value for the comparison will be referred to as the "predetermined value", and in the case of the second summing system (discussed more below) the test value for the comparison will be referred to as the "threshold value"; however, the distinction in terminology is merely to avoid reader confusion, as the "threshold value" may likewise be predetermined. In the case of the example first summing system with a one second window of time, the predetermined value for the comparison is 400 Joules. Thus, in the example first summing system if the summed energy value for the one second time window exceeds 400 Joules, pulsing of the voltage generator is implemented to ensure compliance. However, pulsing the output of the voltage generator is not done according to a fixed method. Whether applied for the short time window (i.e., 20-500 milliseconds) or the long time window (i.e., 1 second), power is interrupted at the time the total summed energy reaches the predetermined threshold value until the end of the then implemented time window, thereby providing an adjusted "time-off" for pulsing.

In some example systems, ceasing of output of the voltage generator may be for a finite amount of time; however, in other example systems the period of time in which energy delivery is ceased is a variable amount of time, which variable amount of time is calculated by the processor 500 of the electrosurgical controller 104. The amount of time in which energy delivery should be ceased as calculated by the processor 500 will be referred to as a quiescent time. As an example, consider the example situation above where 400 Joules are delivered within a one second window, but where the 400 Joules are delivered in the first 0.1 second of the one second window. That is, for 0.9 seconds the voltage generator is off, and then in the last 0.1 second 400 Joules are delivered to the active electrode on the distal tip of the electrosurgical wand. In this example, the energy delivery limit has not been exceeded in the one second window of time; however, if energy delivery continues into the next interval, the energy delivery will exceed the IEC standard 400 Joules in one second. Thus, the controller 104 ceases energy delivery (i.e., turns off the voltage generator) for a quiescent time such that, when energy delivery is resumed, the threshold value will not be exceeded.

Stated again, the example systems and methods calculate a quiescent time representing an amount of time that energy delivery should cease such that energy delivery remains below a certain level. More particularly, the example systems calculate a quiescent time according to the following equation:

$$Q_1 = \frac{E(t_{on})}{t_{on} + t_q} \quad (4)$$

where $Q_1$ is the predetermined value (in Joules per second), $E(t_{on})$ is energy delivered during the generator on time $t_{on}$ (which generator on time $t_{on}$ may be of shorter time length than the window of time over which summing takes place), and $t_q$ is the calculated quiescent time. More precisely, $t_{on}$ is an amount of time that the voltage generator 516 is providing energy to the active electrode(s) during the window of time for the particular summing circuit. Mathematically rearranging the terms:

$$t_q = \frac{E(t_{on})}{Q_1} - t_{on} \quad (5)$$

In the example case of the first summing system with a one second window of time, the $Q_1$ value may be 400 Joules/second (but as will be discussed more below, for further summing systems different Q1 values may be used). Consider again the example first summing system and the example situation where 400 Joules are delivered within a one second window, but where the 400 Joules are delivered in the first 0.1 second of the one second window. In the example, $t_{on}$ will be 0.1 second, $E(t_{on})$ will be 400 Joules, and Q1 will be 400 Joules/second. The controller 104 calculates a quiescent time of 0.9 second. Thus, in order not to exceed the IEC standard 400 Joules in one second energy delivery limitation, the quiescent time in which the voltage generator will be turned off (i.e., not delivering energy) in this example situation is 0.9 seconds.

As mentioned briefly above, at least some embodiments implement two summing systems. The second summing system in accordance with example embodiments integrates and/or sums energy delivery over a smaller yet coextensive window of time. More particularly, in an example system the second summing system integrates and/or sums energy over a window of time spanning 60 milliseconds. In the situation where the energy delivery is calculated in intervals of 1 millisecond, 60 energy delivery values are summed to arrive at the summed energy value for a window of time for the second summing system. Other lengths of time, as well as adjustable lengths of time, may be implemented. The equations above for calculating energy within each interval and calculating a summed energy value are equally applicable to the second summing system, appropriately adjusted for window length and threshold values, and thus the equations will not be repeated again here so as not to unduly complicate the disclosure.

As for the example second summing system, the threshold value against which the summed energy value is tested is reduced in comparison to longer windows of time. For example, the threshold value for the second summing system may be set at 5-400 Joules. Thus, over the window of time for the second summing system (e.g., 20-500 milliseconds), if the summed energy value meets or exceeds the predetermined threshold value for energy delivery, then the energy delivery provided to the active electrode is ceased. As with the first summing system, when the summed energy value meets or exceeds the threshold value of the second summing system, ceasing of energy delivery can be for a fixed period of time, or for a variable amount of quiescent time. The equations above for calculating quiescent time are equally applicable to the second summing system, appropriately adjusted for threshold values, and thus the equations will not be repeated again here so as not to unduly complicate the disclosure.

Having a second summing system may provide for more advantageous operational characteristic of the electrosurgical system in electrosurgical procedures. Consider again the example situation where 400 Joules are delivered within a one second window, but where the 400 Joules are delivered in the first 0.1 second of the one second window. As noted above, such a situation does not result in violation of the IEC standard (so long as the quiescent time of 0.9 second is adhered to). However, a quiescent time of 0.9 second results in 0.9 seconds within which the surgeon cannot ablate tissue, and as such is a very noticeable period of time to a surgeon using the system. The second summing system may thus be considered to better smooth energy delivery and shorten the periods of time in which energy delivery is ceased. In the example situation where the controller 104 attempts to deliver energy at the 400 Watt rate, the second summing system will be triggered, and "pulsing" implemented; however, the amount of time within which energy delivery is ceased for each excursion of summed energy value above the threshold value will be shorter, and thus the electrosurgical system will have a more consistent ablative periods. Depending on the type of tissue treated or type of effect desired, the duration of the second summing window and the energy threshold can be adjusted to allow for very high instantaneous power, or for much smoother power delivery.

Electrosurgical systems operating the example two summing systems noted above (e.g., one second window and 400 Joules, 20-500 millisecond window and 5-400 Joules) provide an operational advantage over related-art systems, which implement "pulsing" when measured current exceeds a particular value. Stated otherwise, systems in which the predetermined value and threshold values are fixed for each window of time provide a significant improvement over related-art systems. However, in yet still further embodiments the threshold value need not be fixed, and indeed may change depending on operational state of the system. For example, the energy delivery rate to establish plasma proximate to the active electrode is in most cases higher than the energy delivery rate needed to maintain previously created plasma. Thus, in some example systems the threshold value may be adjusted depending upon the status of the electrode circuit (which includes the plasma created and maintained in operational relationship to an active electrode of a wand, the fluid between the active and return electrode, and the electrode-fluid interface). The amount of increase and/or decrease of the threshold value is dependent upon many factors, such as the number and size of active electrodes, the type of procedures and desired tissue effect, and aggressiveness in control desired.

It is to be understood that ceasing of energy delivery may be triggered by any summing system standing alone. The summing systems need not agree. For example, the first summing system (one second, 400 Joules) may cause the energy delivery to cease even when the threshold value for the second summing system has not been met or exceeded. Conversely, the second summing system (20-500 milliseconds, 5-400 Joules) may cause the energy delivery to cease even when the predetermined value for the second summing system has not been met or exceeded. Likewise for any additional summing systems implemented, any summing system standing along may cause the energy delivery to cease.

Figure 6:
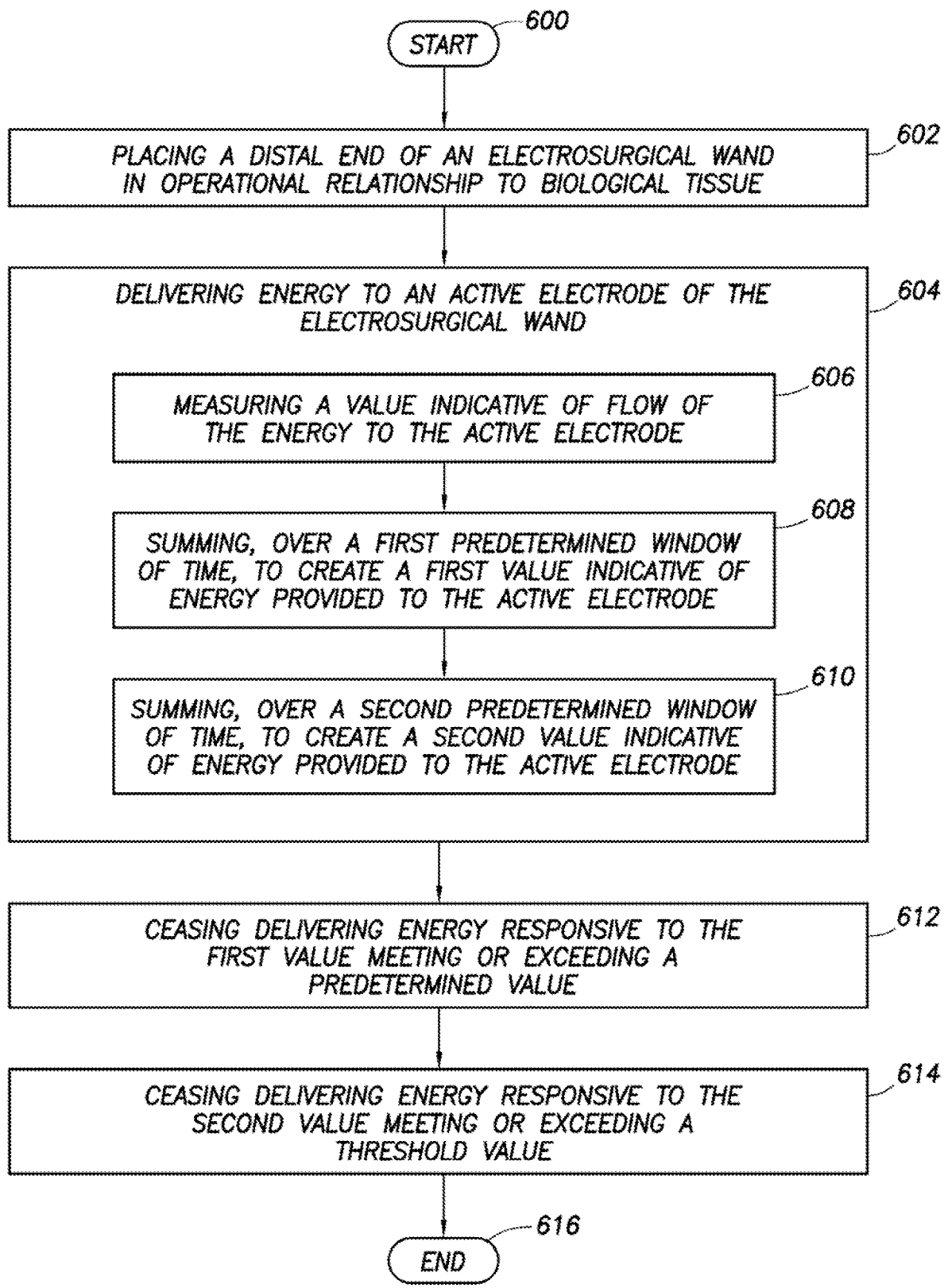
FIG. 6 shows a method in accordance with at least some embodiments.

FIG. 6 shows a method in accordance with example embodiments, some of which may be implemented as a program executed on a processor. In particular, the method starts (block 600) and comprises: placing a distal end of an electrosurgical wand in operational relationship to biological tissue (block 602); and delivering energy to an active electrode of the electrosurgical wand (block 604). During delivering energy, the method may comprise: measuring a value indicative of flow of the energy to the active electrode (block 606); summing, over a first predetermined window of time, to create a first value indicative of energy provided to the active electrode (block 608); and summing, over a second predetermined window of time, to create a second value indicative of energy provided to the active electrode (block 610). Finally, the method may comprise: ceasing delivering energy responsive to the first value meeting or exceeding a predetermined value (block 612); and ceasing delivering energy responsive to the second value meeting or exceeding a threshold value (block 614). Thereafter, the method may end (block 616), in many cases to be immediately restarted.

Figure 7:
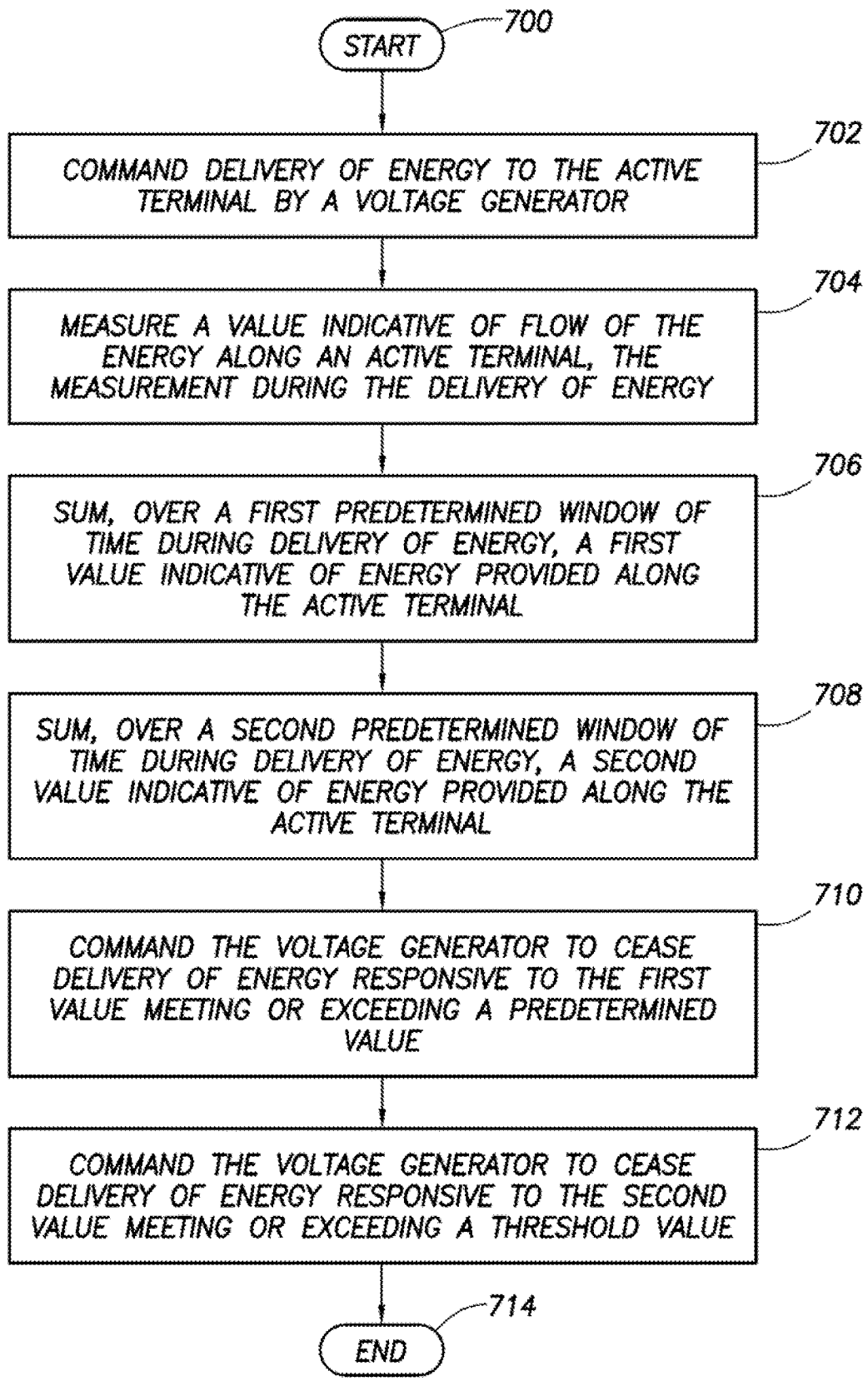
FIG. 7 shows a method in accordance with at least some embodiments.

FIG. 7 shows a method that may be implemented by a program executing on a processor. The method may start (block 700) and comprise: command delivery of energy to the active terminal by a voltage generator (block 702); measure a value indicative of flow of the energy along an active terminal, the measurement during the delivery of energy (block 704); sum, over a first predetermined window of time during delivery of energy, a first value indicative of energy provided along the active terminal (block 706); sum, over a second predetermined window of time during delivery of energy, a second value indicative of energy provided along the active terminal (block 708); command the voltage generator to cease delivery of energy responsive to the first value meeting or exceeding a predetermined value (block 710); and command the voltage generator to cease delivery of energy responsive to the second value meeting or exceeding a threshold value (block 712). The method may end (block 714), in many cases to be immediately restarted.

The above discussion is meant to be illustrative of the principles and various embodiments of the present invention. Numerous variations and modifications are possible. It is intended that the following claims be interpreted to embrace all such variations and modifications.

From the description provided herein, those skilled in the art are readily able to combine software created as described with appropriate general-purpose or special-purpose computer hardware to create a computer system and/or computer sub-components in accordance with the various embodiments, to create a computer system and/or computer sub-components for carrying out the methods of the various embodiments and/or to create a non-transitory computer-readable media (i.e., not a carrier wave) that stores a software program to implement the method aspects of the various embodiments.

While preferred embodiments of this disclosure have been shown and described, modifications thereof can be made by one skilled in the art without departing from the scope or teaching herein. The embodiments described herein are exemplary only and are not limiting. Because many varying and different embodiments may be made within the scope of the present inventive concept, including equivalent structures, materials, or methods hereafter thought of, and because many modifications may be made in the embodiments herein detailed in accordance with the descriptive requirements of the law, it is to be understood that the details herein are to be interpreted as illustrative and not in a limiting sense.

What is claimed is:

1. An electrosurgical method comprising:
placing a distal end of an electrosurgical wand in operational relationship with biological tissue;
delivering energy to an active electrode of the electrosurgical wand, and while delivering the energy:
measuring a value indicative of flow of the energy to the active electrode;
summing the value, over a first predetermined window of time, to create a first value indicative of a summed energy provided to the active electrode;
summing the value, over a second predetermined window of time, to create a second value indicative of a second summed energy provided to the active electrode, the second predetermined window of time being different than the first predetermined window of time, and the second predetermined window of time coextensive with the first predetermined window of time; and
ceasing delivering the energy responsive to the first value meeting or exceeding a threshold value, and/or the second value meeting or exceeding a predetermined value, wherein the first predetermined window of time and/or the threshold value is adjustable to allow for differing electrosurgical effects on the biological tissue.

2. The electrosurgical method of claim 1 wherein measuring the value further comprises measuring at least one value selected from the group consisting of:
a value indicative of electrical current provided to the active electrode, a value indicative of root mean square (RMS) electrical current provided to the active electrode, a value indicative of voltage provided to the active electrode, and a value indicative of RMS voltage provided to the active electrode.

3. The electrosurgical method of claim 1 further comprising: wherein summing the value, over the first predetermined window of time, further comprises summing the value over a 20-500 millisecond window; and wherein summing the value, over the second predetermined window of time, further comprises summing the value over a one second window.

4. The electrosurgical method of claim 3 wherein the threshold value is 5-400 Joules; and the predetermined value is 400 Joules.

5. The electrosurgical method of claim 1 wherein ceasing delivering the energy responsive to the first value meeting or exceeding a threshold value further comprises calculating a first quiescent time, the first quiescent time representing an amount of time remaining in the first predetermined window of time and resuming delivering the energy to the active electrode once the first quiescent time is complete.

6. The electrosurgical method of claim 5 wherein ceasing delivering the energy responsive to the second value exceeding the predetermined value further comprises:
calculating a second quiescent time representing an amount of time within which delivering the energy should cease; and ceasing delivering the energy for the second quiescent time.

7. The electrosurgical method of claim 1 further comprising:
increasing the threshold value and/or first predetermined window of time to adjust for the electrosurgical effect corresponding with a higher instantaneous power; and
decreasing the threshold value and/or first predetermined window of time to adjust for the electrosurgical effect corresponding with a smoother power delivery.

8. An electrosurgical controller comprising:
a processor;
a memory coupled to the processor;
a voltage generator operatively coupled to the processor, the voltage generator comprising an active terminal also coupled to the processor;
the memory configured to store a program that, when executed by the processor is configured to cause the processor to:
command delivery of energy to the active terminal by the voltage generator;
measure a value indicative of flow of the energy along the active terminal, the measurement during the delivery of the energy;
sum the value, over a first predetermined window of time during the delivery of the energy, to create a first value indicative of a first sum of the energy provided along the active terminal; and
command the voltage generator to cease the delivery of the energy responsive to the first value meeting or exceeding a threshold value; and
wherein the first predetermined window of time and/or the threshold value is adjustable to either:
increase a pulse rate and provide the delivery of the energy more smoothly by decreasing the threshold value and/or first predetermined amount of time; or
slow the pulse rate and allow a higher instant power by increasing the threshold value and/or first predetermined amount of time.

9. The electrosurgical controller of claim 8 wherein the program is further configured to cause the processor to:
sum the value over a second predetermined window of time during the delivery of the energy, to create a second value indicative of a second sum of the energy provided from the active terminal, the second predetermined window of time having a different length than the first predetermined window of time, and the second predetermined window of time coextensive with the first predetermined window of time; and
command the voltage generator to cease the delivery of the energy responsive to the first value meeting or exceeding the threshold value or the second value meeting or exceeding a predetermined value.

10. The electrosurgical controller of claim 9 wherein, the program is further configured to cause the processor to:
calculate a quiescent time upon commanding the voltage generator to cease the delivery of the energy responsive to the second value meeting or exceeding the predetermined value, the quiescent time representing an amount of time within which the delivery of the energy should cease; and
command the voltage generator to cease the delivery of the energy for the quiescent time.

11. The electrosurgical controller of claim 8 wherein the value indicative of flow of the energy is at least one value selected from the group consisting of: a value indicative of electrical current flow along the active terminal, a value indicative of root mean square (RMS) electrical current along the active electrode, a value indicative of voltage provided by the active terminal, and a value indicative of RMS voltage provided by the active terminal.

12. The electrosurgical controller of claim 8 wherein the first predetermined window of time has a length of 20-500 milliseconds; and wherein the second predetermined window of time has a length of one second.

13. The electrosurgical controller of claim 12 wherein the threshold value is equal to or less than 5-400 Joules and the predetermined value is equal to or greater than 400 Joules.

14. The electrosurgical controller of claim 8 wherein the program is further configured to cause the processor to:
calculate a quiescent time while commanding the voltage generator to cease the delivery of the energy, the quiescent time representing an amount of time within which the step of commanding the delivery of the energy should cease; and
cease the delivery of the energy for the quiescent time.

15. A non-transitory computer-readable medium configured to store a program that, when executed by a processor is configured to cause the processor to:
command delivery of energy to an active terminal of a voltage generator;
measure a value indicative of flow of the energy along the active terminal, while delivering the energy;
sum the value over a first predetermined window of time while delivering the energy, resulting in a first value indicative of a summed energy provided along the active terminal;
sum the value over a second predetermined window of time while delivering the energy resulting in a second value indicative of a second summed energy delivered along the active terminal, the second predetermined window of time being a longer length than the first predetermined window of time, and the second predetermined window of time coextensive with the first predetermined window of time; and
command the voltage generator to cease the delivery of the energy responsive to the first value meeting or exceeding a threshold value, or the second value meeting or exceeding a predetermined value; wherein the first predetermined window of time and/or the threshold value is selectable to allow for differing tissue effects with differing interruption to the delivery of the energy.

16. The non-transitory computer-readable medium of claim 15 wherein the program is further configured to cause the processor to:
calculate a first quiescent time while commanding the voltage generator to cease the delivery of the energy responsive to the first value meeting or exceeding a threshold value, the first quiescent time representing an amount of time remaining in the first predetermined window of time; and
command the processor to resume the delivery of the energy once the first quiescent time is complete.

17. The non-transitory computer-readable medium of claim 15 wherein the processor is further configured to:
calculate a second quiescent time while commanding the voltage generator to cease the delivery of the energy responsive to the second value meeting or exceeding the predetermined value, the second quiescent time representing an amount of time within which the delivery of the energy should cease; and command the processor to resume the delivery of the energy on completion of the second quiescent time.

\* \* \* \* \*